United States Patent [19]
Lemelson

[11] Patent Number: 5,865,744
[45] Date of Patent: Feb. 2, 1999

[54] METHOD AND SYSTEM FOR DELIVERING THERAPEUTIC AGENTS

[76] Inventor: Jerome H. Lemelson, 930 Tahoe Blvd, Incline Village, Nev. 89451-9436

[21] Appl. No.: 714,211

[22] Filed: Sep. 16, 1996

[51] Int. Cl.$^6$ ...................................................... A61B 6/00
[52] U.S. Cl. .......................... 600/407; 600/437; 606/130; 901/2; 128/922; 378/62
[58] Field of Search ................................. 128/653.1, 920, 128/922, 660.03; 606/130; 901/1, 2, 8, 6; 382/153, 194, 195, 128; 378/4, 62, 205; 600/407, 439, 437

[56] References Cited

U.S. PATENT DOCUMENTS

| | | | |
|---|---|---|---|
| 4,653,109 | 3/1987 | Lemelson et al. | 382/34 |
| 4,671,256 | 6/1987 | Lemelson | 128/1.1 |
| 5,078,140 | 1/1992 | Kwoh | 128/653.1 |
| 5,397,323 | 3/1995 | Taylor et al. | 606/130 |
| 5,408,409 | 4/1995 | Glassman et al. | |
| 5,441,505 | 8/1995 | Nakamura | 606/130 |
| 5,464,013 | 11/1995 | Lemelson | 128/653.1 |
| 5,542,028 | 7/1996 | Minami | 395/86 |
| 5,553,198 | 9/1996 | Wang et al. | 395/80 |
| 5,572,999 | 11/1996 | Funda et al. | 128/653.1 |
| 5,622,170 | 4/1997 | Schulz | 128/653.1 |

*Primary Examiner*—Marvin M. Lateef
*Assistant Examiner*—Shawna J. Shaw

[57] ABSTRACT

A system and method are disclosed for internally delivering a therapeutic agent to a patient under the automatic control of a computer. A diagnostic imaging modality, such as a CAT or MRI scanning system, generates one or more images of the patient's anatomy showing an anatomical region into which it is desired to deliver the cellular transplants. For each such image, location coordinates with respect to a patient support means are calculated by the computer for each individual pixel making up the image. Location coordinates are then defined for a select body region corresponding to pixels of the anatomical image(s) designated by a user of the system to receive the therapeutic agent. The computer then operates a manipulator arm in order to position an injection tool such as an injection needle or catheter mounted on the arm adjacent to the select body region. In the case of an injection needle, the needle is inserted into the region at the appropriate depth, and an injector is operated under computer control to force a predetermined amount of a medium containing the therapeutic agent out of a lumen within the injection needle and into the select body region.

16 Claims, 2 Drawing Sheets

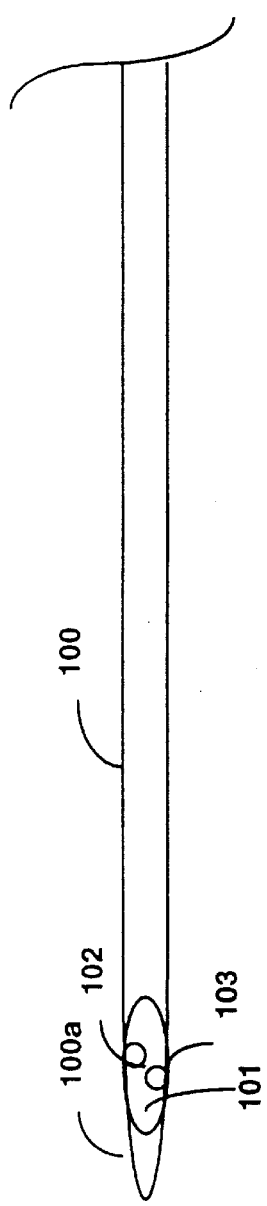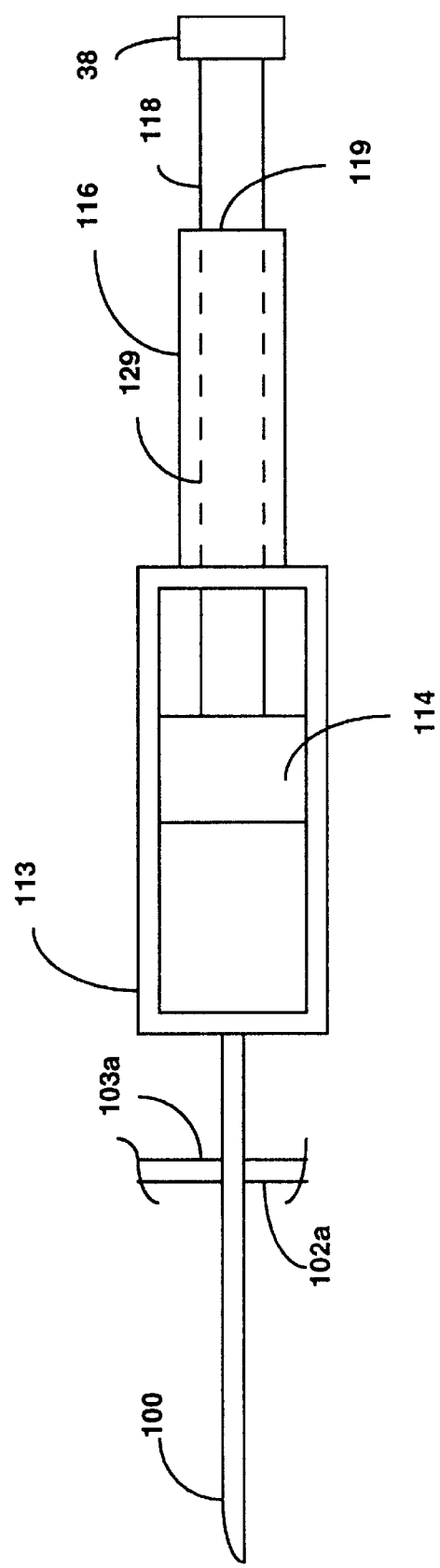

METHOD AND SYSTEM FOR DELIVERING THERAPEUTIC AGENTS

BACKGROUND AND SUMMARY OF THE INVENTION

The present invention is a method and system for introducing therapeutic agents into living beings in a controlled manner which permits such agents to be directed to a particular locality with a high degree of precision. Such therapeutic agents, which may be used to advantage with the system, include chemotherapeutic drugs, genetic material, living cells introduced for transplantation, and other biological therapeutic agents requiring localization to target tissue for optimum effect.

In accordance with the invention, a computer controlled injection needle is employed to inject a therapeutic agent into select target tissue of a patient, for example, a tumor. The tumor is located using one or more scanning modalities capable of distinguishing the target tissue such as plain view X-ray, computerized axial tomography X-ray (CAT scanning), magnetic resonance imaging (MRI scanning), positron emission tomography (PET scanning), and ultrasound scanning. Once the target tissue is located and its borders defined by the imaging modality, location coordinates are generated and assigned with respect to a support structure supporting the patient. A manipulator arm assembly under computer control is used to move and operate the injection needle. A stored program, having user defined parameters and the location coordinate data, then directs the injection needle to a plurality of sites on the patient's body at corresponding insertion depths which result in positioning the tip of the injection needle into the target tissue at various locations. The therapeutic agent is then injected in controlled amounts at each such injection location. In this manner, the agent may be delivered to the target tissue with greater precision than with prior methods so that less of the therapeutic agent is delivered to non-target tissue where its effects may be deleterious.

The present invention may also be employed with therapeutic agents for effecting tissue engineering, that is the selective growth of various cell types within a target tissue of a patient. One such embodiment uses an agent comprising a growth factor or cytokine in conjunction with another agent for creating specificity. A growth factor may then be employed to cause the selective growth of specific living tissue via cellular proliferation without causing the undesired proliferation of other cell types normally responsive to the growth factor. Growth factors which can be used with such method include those of broad specificity such as EGF, PDGF, fibroblast growth factors (FGFs), hepatocyte growth factor (HGF), insulin, insulinlike growth factor (IGF-1), nerve growth factor (NGF), vascular endothelial growth factor (VEGF), and macrophage colony stimulating factor (M-CSF). Such method may be useful not only in treating certain disease states where specific cellular proliferation is of value, but also in enhancing the production of animal products such as milk from dairy cattle and various hormones from genetically engineered animals.

In order to produce such a selective growth agent, a specific growth factor or other cytokine is selected which elicits a desired response (eg., cellular proliferation) in a specific target cell of a multicellular organism. Monoclonal antibodies are then produced which have a specific binding affinity for other cells of the organism that also respond to the growth factor, which other cells are referred to herein as non-target cells. Such monoclonal antibodies are directed toward antigenic determinants that are expressed by non-target cells but not by target cells. The monoclonal antibodies are then conjugated with a protein corresponding to the extracellular domain of the growth factor receptor. In order to eliminate the response of the non-target cells to the growth factor, the monoclonal antibody conjugate is administered together with the growth factor by employing the computer controlled injection needle apparatus as described above. The antibody conjugate then binds to the non-target cells and presents a binding site for the growth factor that results in competitive inhibition of the growth factor's binding to the cell's native growth factor receptor. The target cells, on the other hand, are left fully responsive to the growth factor. The method may also be combined with other techniques for causing tissue growth such as electrical stimulation, used presently for promoting bone healing, as well as specific nutrients needed for cell growth.

Another way to effect tissue engineering is to transplant cells into a target tissue. Certain disease states involving organ failure can be successfully treated by replacing only a small proportion of the organ mass with populations of donor cells. Such donor cells (referred to herein as "cellular transplants") are obtained, for example, from a donor organ by mechanical disruption or enzymatic digestion of the parenchyma of the donor organ. Advances in cell culture techniques have made it possible to maintain donor cells, such as hepatocytes, in a viable and functional state in vitro for extended periods of time until they are transplanted into a recipient. Successful transfer of such cellular transplants into animal recipients has recently been demonstrated for both liver cells (See Rhim et al., *Science* 263, 1149 (1994)) and heart muscle cells (See Soonpaa et al., *Science* 264, 98 (1994)).

In order to fully realize the advantages of cellular transplantation, the transplant procedure should be performed in a minimally invasive manner without the requirement of a surgical operation. Placement of the cellular transplants into the correct anatomic location, however, is critical if the cellular transplants are to function properly after implantation. The present invention is a system and method for accomplishing such objectives.

In accordance with the present invention, a transplantation tool (which may be, for example, an injection device such as a hypodermic injection needle or a catheter for delivering cellular transplants through an outflow port to an intraductal or other internal body site within which the catheter is disposed) is manipulated by a manipulator or motor-driven catheter under computer control so as to deliver a predetermined amount of a fluid transplant medium containing cellular transplants to a select anatomical area of a patient's body as defined by location coordinates locating the select body area with respect to a structure supporting the patient. In one embodiment of the invention, the transplantation tool is mechanically positioned by a robotic arm operating automatically in accordance with imaging information derived from a scanning system and fed to a computer. In other embodiments, the transplantation tool is positioned manually by an operator while a computer monitors the operation to provide a computer generated indication of when the tool is operatively positioned so as to effect the injection or other delivery of the transplant medium at a selected coordinate location of the body into select body or organ tissue thereof.

It is therefore a primary object of the present invention to provide a system and method for precisely delivering therapeutic agents to a patient at selected anatomical locations.

It is a further object to provide a computerized method and system that enables user designation of selected anatomical locations for cellular transplant delivery via image signals generated by imaging devices which image signals are stored in a computer and displayed to the user.

It is a further object to provide a system and method that automatically delivers cellular transplants to user selected locations under computer control.

Other objects, features, and advantages of the invention will become evident in light of the following detailed description considered in conjunction with the referenced drawings of a preferred exemplary embodiment according to the present invention.

BRIEF DESCRIPTION OF THE DRAWINGS

FIG. 2 shows the tip an injection needle having lumens for delivery of the selected therapeutic agent into the injection site as well as additional medical agents.

FIG. 3 shows an injection assembly for use in delivering precise amounts of a therapeutic agent through an injection needle.

DETAILED DESCRIPTION OF THE INVENTION

A. General

Figure 1:
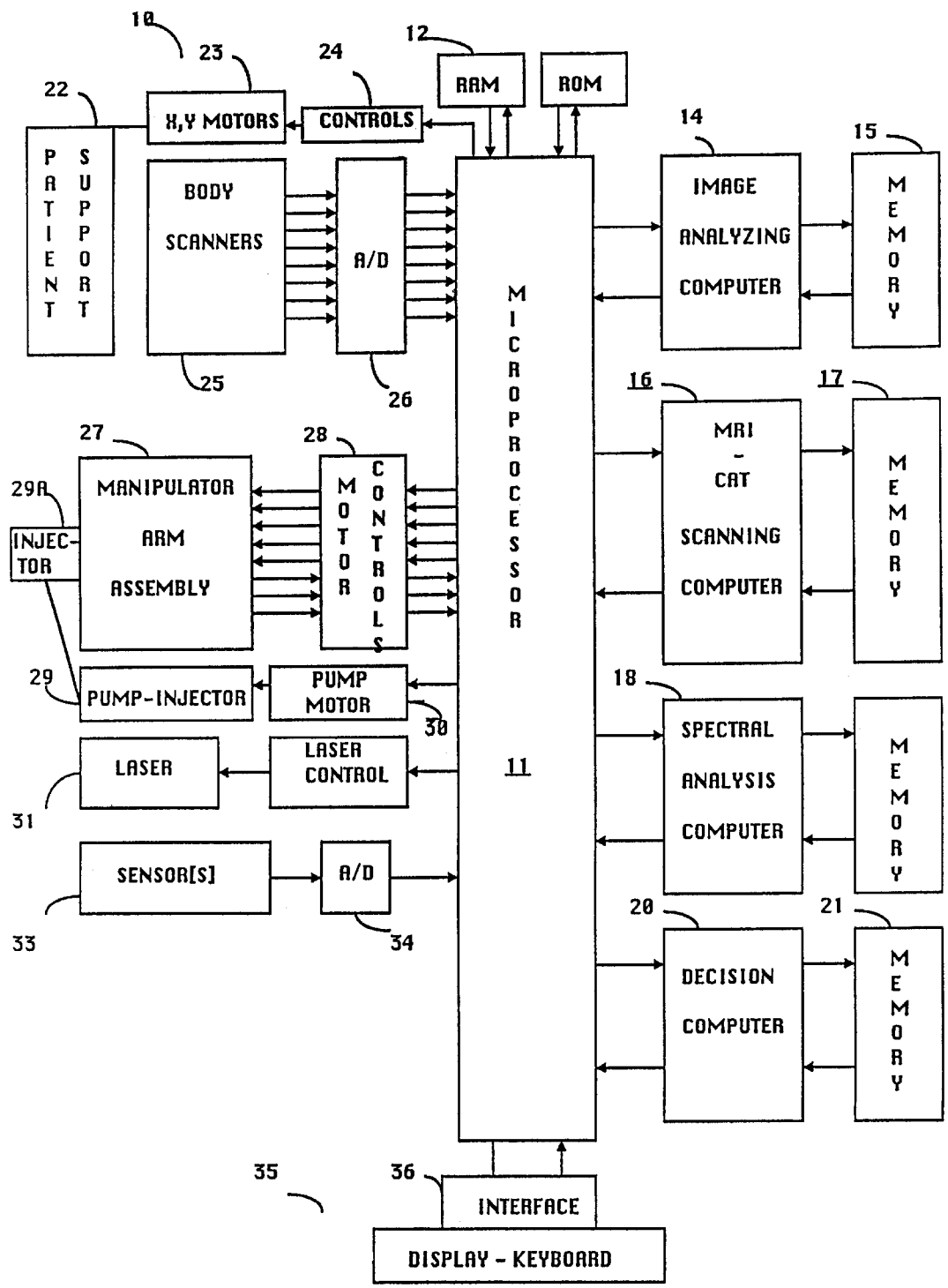
FIG. 1 is a schematic diagram of an exemplary system for delivering therapeutic agents in accordance with the present invention.

The location coordinates of select tissue of a living being into which select tissue a therapeutic agent (such as a drug, genetic material, a selective growth factor composition, or a transplant medium containing cellular transplants) is to be injected are defined or computed with respect to images of the patient's anatomy defining anatomical structures which may be generated, for example, by employing computerized axial tomography (CAT scanning), magnetic resonance imaging (MRI), ultrasonography, PET, infrared or microwave imaging, or other types of electronic scanning. In accordance with the present invention, a computer image of a select anatomical area is generated by using one or more of such conventional imaging modalities. A location coordinate with respect to a patient support structure is assigned to each pixel making up the image. The antatomical region into which it is desired to deliver the therapeutic agent is then located on the electronically generated image or images by a radiologist, for example, with selected of the pixels making up the image of the region serving to define the transplant location. A preferred means by which this can be performed is to display the images on a display monitor having a manually positionable cursor for outlining an area containing the lesion. The operator of the system then inputs to a computer digital data in the form of codes defining the anatomical location to which a cellular transplant or transplants are to be delivered as represented by the select pixels within the outlined area. As described below, each pixel of the body or organ image displayed by the computer has assigned to it a set of location coordinates calculated or defined with respect to a structure, such as a table supporting the patient, while the imaging is performed. The same or a similar patient support structure is then utilized during the injection procedure, the injector or injection needle is carried in movement by the manipulator or catheter under computer control, inserted into select tissue, and operated so as to deliver the agent to select location coordinates with respect to the support structure. In a typical embodiment, a first computer program calculates the location coordinates of select body regions as defined by pixels of images produced by an imagining device using coded signals representing the sensed relative prositions of the patient support in the imaging device, while a second computer program calculates the location coordinates of the injection needle and determines when the needle is located in the select body region into which it is desired to deliver the therapeutic agent.

In one form, the patient is required to be in the same position with respect to the support structure during both the imaging and injection procedures so that the location coordinates selected will correspond to the proper anatomical region of the patient. One way of accomplishing this is to use a patient support structure having a moldable support structure defining a surface that can be made to conform to the shape of the patient's body as a kind of body cast. Once such a body impression is made, the patient may be placed in substantially the same position on the support structure for both scanning/imaging and subsequent transplantation procedures. Such a moldable patient support may also serve to immobilize the patient during both procedures. Other patient retraint devices, such as straps and adjustably positionable table stops, may also be employed.

The manner of assigning location coordinates to each image pixel depends upon the particular imaging modality. For example, with a conventional CAT scanner, the x-ray tube emits a narrow beam of x-rays toward the patient with an x-ray detector, such as an array of scintillation detectors, positioned on the opposite side of the patient on which an x-ray shadow is formed. The x-ray tube and detectors, mounted on a rigid gantry, are rotated in multiple steps about the body until an entire axial slice is viewed from multiple angles. Codes defining the data acquired by the scintillation detectors are entered into a computer which uses mathematical algorithms operable to reconstruct a cross-sectional image of the region examined. Such a computerized scanning arrangement calculates the degree to which the tissue interposed between the x-ray tube and the detectors absorb the x-ray beam and thereby provides an attenuation coefficient for each area of tissue examined. Essentially, the quantity of x-rays absorbed in small volumes(voxels) of body tissue in the slice is computed. Computer analysis of the data collected then allows assignment of a numerical value to each small area (pixel) of the cross-sectional plane. By means of a digital-to-analog converter, the numerical value of each pixel is translated to a gray scale value for driving a CRT display or the like.

Due to the nature of the CAT scanning image reconstruction algorithm, the computer necessarily must assign location coordinates to each pixel with respect to the x-ray detector in order to generate the displayed image. Such coordinates are computed with respect to the patient support structure in the axial plane which is being imaged. In order for such coordinates to be useable for properly directing a transplantation tool in accordance with the present invention, however, they must be scaled and combined with another cooordinate along the axial axis. In order to assign an axial location coordinate with respect to the patient support structure for each pixel, the positions of the x-ray tube and detector with repect to the patient support surface are sensed, and digital signals are generated that are input to the computer during the imaging procedure. The location coordinates for each pixel making up the image with respect to the patient support structure may be then readily calculated.

In pulse-echo ultrasound techniques, an ultrasonic pulse is transmitted through the body tissues with the reflected echoes from each acoustical interface sensed by a transducer in order to provide a train of digital signals that define an image of the underlying structure. In so-called B-mode ultrasound, the pulse-echo procedure is performed in a scanning manner to provide signals for imaging the underlying morphologic structures in a tomographic format. The resulting scanning signals, after digitization, are used by electronic circuitry to construct a two-dimensional array of pixel values for driving a display. In order to construct an image, each pixel is assigned a coordinate location with respect to the transducer in the same plane at which the ultrasound is emitted. Conventional ultrasonic scanning, transduc requires that the ultrasonic transducer be contacted or coupled to the body surface over the region to be examined and positioned so as to scan at various angles. In order for the computer to compute the location coordinates for each pixel making up a display of an ultrasonic scan, the transducer is mounted on a movable arm having sensors in its joints for producing signals proportional to the degree of flexion or rotation of each such joint, which sensors generate signals that are then fed to the computer for calculating the arm's position and orientation. Using appropriate scaling factors, the location coordinates for each pixel making up the image with respect to the patient support means may be readily calculated by a computer supplied with the above-mentioned data.

Computerized image construction in conventional MRI scanning, for employment in the present invention, is similar to that used in CAT scanning in that intensity values for an array of pixel values are computed with each pixel value stored in the computer being assigned a set of location coordinates in order to generate the image. In MRI scanning, nuclei such as protons are subjected to a magnetic field gradient, called the slice-select gradient, which varies along the axis perpendicular to the plane of the image. Certain protons (such as hydrogen nuclei of water molecules in the tissue being scanned) within the magnetic field gradient are excited to resonance by a so-called 90 degree RF pulse which causes them to emit detectable radiation. The amplitude and frequency of such emitted radiation is used to assign proton density values to pixels and generate the MRI image. The location coordinates of each pixel in the image are calculated with respect to the patient support structure within the plane of the image cross-section, assuming the receiver coil of the MRI scanner remains at a fixed distance from the patient support structure. In order to derive an axial coordinate value (ie., along an axis perpendicular to the plane of the cross-sectional image) for each pixel, it is necessary for the computer to compute the distance along the slice-select gradient with respect to the patient support structure where the Larmor frequency of the excited nuclei corresponds to the frequency of the 90 degree RF pulse. Such a computation only requires that the computer be supplied with data reflecting the magnitude of the slice-select gradient field versus distance and the frequency of the RF pulse, which can either be assumed to be in accordance with computer command or can be sensed by magnetometers and a separate RF receiver coil. MRI scanners also allow the particular gradient fields to be generated along arbitrarily chosen axes so as to produce images not only in the transverse plane, but also in coronal, sagittal, and oblique planes. The axial coordinate for each image is then computed in the same way as just described, but the coordinate is then along an axis perpendicular to the plane of the cross-sectional image. Finally, since the patient support structure and the MRI imaging apparatus are relatively moveable with respect to one another, the computer is fed data produced by position sensing means so that the location coordinates can be translated so as to be with respect to the patient support structure.

Once the location coordinates defining the select body region into which it is desired to inject the cellular transplants have been calculated by the computer, a manipulator arm on which is mounted an injection needle is moved to the select body region under computer control. The injection needle is then inserted into the select body region at an insertion site on the surface of the body, and a predetermined amount of a transplant medium is injected into such region. The process may then be repeated at different needle insertion depths for the same insertion site and/or at different insertion sites in the select body region. As will be described more fully below, electro-optical sensing and monitoring means may be provided allowing the effects of the injection to be monitored by the computer so that the results of such monitoring may be used to control further injections.

B. System description

FIG. 1 shows a system 10 for effecting the automated performance of a controlled injection procedure in accordance with the present invention. The therapeutic agent may be delivered internally to a patient by injection where a hollow tube or needle, such as a hypodermic needle, is automatically positioned with respect to the patient by means of a multiple axis electro-mechanical manipulator which is controlled in its operation by coded control signals generated as a result of scanning that portion of the patient's body where it is desired for the agent to be delivered. A catheter for delivering a therapeutic agent mounted to a manipulator may be similarly directed under computer-control to an intraductal or other internal body site.

The scanning signals may be generated by one or more known scanning systems such as a nuclear magnetic resonance (NMR or MRI) scanning system, a computerized axial tomography (CAT) scanning system employing X-ray scanning, a positron emission tomographic (PET) scanning system, various infrared scanning systems operable to generate image signals of tissue and bones, or ultrasonic pulse-echo scanning systems. Such scanning signals may be computer processed and analyzed to generate multiple cross-sectional views of the portion of the body where it is desired to deliver the therapeutic agent. The image information defined in the cross-sectional views or slices of the body tissue may be digitized to generate trains of digital (picture) signals which are analyzed by a computer wherein resulting code signals are generated defining the borders or peripheries of the select anatomical structures and which may be further computer processed to provide further code signals indicative of coordinate locations of those structures. Such coded information may be used by the computer to control the operation of an automatic multi-axis manipulator for a surgical or treatment device, such as a hypodermic needle and a motorized pump, to automatically position and cause the needle to directly penetrate the skin and to pass through tissue aligned with and including the tissue where it is desired to inject an agent. After and/or during such penetration of tissue, the computer controls the operation of a pump motor and/or valve actuator solenoid to cause a select amount of a therapeutic agent to enter the tissue.

The medical procedure described above may be applied once or repeated a number of times without surgery or may supplement surgery which may also be computer controlled by one or more surgical devices such as powered cutting tools, blades positioned and moved in cutting operations by the computer controlled manipulator, nozzles generating high velocity jets of liquid medication(s), one or more lasers generating a beam or beams of tissue penetrating surgical radiation or other surgical device(s) supported and operatively moved by the manipulator.

System 10 includes a number of computers, devices and subsystems which are automatically controlled in their operation or generate feedback information in the form of signals passed through a control computer or microprocessor 11. An image analyzing computer 14 with an attendant programmable memory 15 analyzes image information generated by an NMR or CAT scanning computer 16 with attendant memory 17 which receives digitized image information from a plurality of MRI sensors 25 which scan a select portion of the body of a patient held immovable against a patient support or table 22 which is motorized and driven in multi-axis movement by a plurality of gear motors 23, the controls 24 of which are operated by trains of digital control signals passed through microprocessor 11 from either manual controls and/or one of the computers connected to the microprocessor. While conventional CAT and MRI scanning arrangements generally rotate and axially move the patient through the scanning field, the MIR, CAT, PET body scanners or array of sensors 25 may also be supported on a mount which is motor driven and controlled to move about or along one or more axes by means of a computer such as a decision computer connected to the microprocessor and operable to analyze the signals output by one or more of the computers 14 and 16 to effect control of the treatment operation and/or at least a portion of the scanning operation. The analog image signals output by the body scanners are converted to trains of digital image signals by one or more analog-to-digital converters 26 which pass such trains of signals through microprocessor 11 to the MRI or CAT scanning computer 16 for analysis and conversion to usable image information for use by the image analyzing computer 14.

In the preferred embodiment, a manipulator arm assembly 27 of conventional design is supported adjacent the patient support 22 to which it is preferably connected. The plurality of articulated arms of the multi-axis manipulator are operated by respective reversible gear motors (not shown) which are controlled in their operations by a bank of controls 28 which receive and pass direct command control signals from the computer 20 and apply feedback signals from the manipulator motors to effect a suitable degree of precision operation of the manipulator to selectively position its operating head and surgical device such as a laparscope and/or injection needle in alignment with select tissue to be treated or operated on.

In FIG. 1, the manipulator 27 has an operating head 29A containing an elongated tube or hypodermic-type needle supported thereby and operable to be driven by the controlled operation of one or more of the motors driving the manipulator 27 or a separate motor supported by the operating head to force the injection needle through body tissue located by the scanning system. A pump motor 30 drives a pump 29 when its control input is operated by a start-signal received from computer 20 after the manipulator 27 has been controlled to position the injections needle in alignment with the injection location and the needle has penetrated the tissue.

A sensor or sensor array 33 may be located on the manipulator head or injector assembly 29A and may be operable to receive light reflected from tissue adjacent the end of the injection needle. An optical fiber light pipe may extend from the output of the laser 31 through and to the open end of the injection tube or needle to conduct laser light to tissue adjacent the open end of the needle while a second optical fiber may extend from such open end, back up another light pipe in the needle to the sensor 33. An additional lumen in the needle may be used to permit a liquid drug to pass down along the needle or tube and into select tissue penetrated by the needle. Resulting spectral radiation emitted by the tissue intersected by the laser radiation is passed to the end of the optical fiber adapted to receive same and back along such fiber to the photodetector at the other end thereof which generates an analog electrical signal modulated with spectral information relating to the tissue intersected by the laser light.

Also shown connected to the control computer or microprocessor 11 via an interface 36 is a computer 35 such as a workstation or PC which includes a display and a keyboard which is operable to input data to the RAM 12 or any of the computers 14, 16, and 18 or to control the operation of the manipulator 27, pump motor 38 and laser 31 or a plurality of such subsystems and devices for performing the described treatment or surgical operations. It is noted that the pump 29 may be varied in its operation in accordance with the control signals generated by the decision computer 20 to a controller for such motor to predetermine the quantity and rate of flow of transplant medium or medication pumped to the injector 29A after its injection tube or tubular needle has been driven under computer control to a select location with respect to select tissue. A plurality of pumps, such as pump 29, are operated by respective pump motors may be provided mounted on the operating head of the manipulator, each of which pumps is operable to force flow a different medical material from a respective of a number of reservoirs to the needle or tube of the injector 29A.

System 10 may also be operable to automatically perform auxilliary or other operations on select tissue such as select tissue manipulation, handling, or cutting operations using one or more automatically positioned and controlled grippers or cutting tools which are supported by the operating head of the manipulator 27 and controlled in powered operation to cut select tissue or employing one or more lasers to ablate, burn or otherwise operate on such select tissue. Such surgical operations may be effected per se or in combination with the described selective injection of a therapeutic agents in accordance with location information derived from one or more of the described scanning techniques.

A modified form of system 10 may also employ a computer controlled manipulator operable to (a) insert and drive a catheter into or through a body duct, (b) effect a small opening in a select portion of skin or other body tissue and insert a surgical instrument such as a laparoscrope therethrough and power drive same in one or more of a plurality of operations on and with respect to select tissue within the body, which operations may include forcing an injection needle from the tube of the instrument to cause it to penetrate and inject a select amount of therapeutic agent as described into select tissue. Such operations may also include the application of laser light energy, as described, to inspect and/or operate on select tissue deep in the body and one or more micromanipulators to hold or manipulate select tissue during the surgical operations.

Not shown, but assumed to form part of the computer 35 and its peripheral controllers, are manual means for effecting selective control of the described manipulators and the body tissue scanning devices, for use by medical personnel in supplementing the computer controlled operations in the performance of certain operations to detect and treat select tissue of the body. Computer controlled imaging and laser range finding devices may also be employed to provide scanning signals for computer 14, to permit the computer to further analyze the image content defined by select cross-sectional views or slices generated by the CAT or MRI scanning system 25 so as to automatically determine the depth location and three dimensional shape of the injection site and to provide coded control signals for effecting automatic surgery on select tissue or treatment as described. Thus the body scanning system 25 may be employed per se to generate computer analyzable image information or may be supplemented with image information generated by an electronic camera such as a television camera and/or by one or more laser-photodetector scanning arrangements which are fixedly supported adjacent the patient support, supported to move with the manipulator of the scanners of system 25 and/or supported on the head of the automatic manipulator 27 or by a separate manipulator (not shown).

C. Injector description

FIG. 2 depicts the tip of an injection needle 100 (that may be, for example, of approximately 30 gauge size) in accordance with the present invention. A sharp tip 100a allows the needle to puncture skin and other tissue and to be driven to a select depth into a select body region. Disposed within the needle is a lumen 101 for delivering a drug or other agent to the tissue in which the needle is inserted. Also disposed within the needle are additional lumens 102 and 103. In one embodiment, the lumens 101 and 102 may be used to inject additional medical agents such as collagen into the injection site. In other embodiments, the lumens 102 and 103 may contain optical waveguides for transmitting light to the tissue for therapeutic or diagnostic purposes. Such waveguide may consist of an optical fiber supported within a passageway or may be a waveguide consructed integral with the needle. In the latter case, a light transmissive core of one refractive index is surrounded along the length of the needle by material of another refractive index so as to constitute a cladding and enable the transmission of electromagnetic radiation. Such radiation may be laser radiation generated by laser 31 used used to perform a surgical procedure, or may be other types of therapeutic radiation. If the light radiated from the waveguide is to be used for diagnostic purposes, a second waveguide disposed within lumen 103 of needle 100 captures the radiation emitted from the first waveguide after it has been scattered or reflected by tissue components such as cells, subcellular organelles, molecules, or other structures. Such light is transmitted by the second waveguide to photodetector 33 and analyzed by spectral analysis computer 18.

FIG. 3 shows an exemplary injector 29 for delivering a controlled amount of a transplant medium or other agent to the select tissue through conduit 101. The injector 29 comprises a syringe 113 for containing a quantity of the medium to be injected and connected to needle 100. A plunger or piston 114 moves through the barrel of the syringe 113 to displace the fluent medium into conduit 101 from where the medium is injected into the selected tissue site. Also shown connected to needle 100 are a conduit 103a for connecting to lumen 103 and a conduit 102a for connecting to lumen 102 of needle 100. The injector 29 is mounted on manipulator arm 27 so as to be movable and positionable under computer control. In order to for the injector to deliver controlled amounts of the therapeutic agent under the control of microprocessor 11, the linear motion of plunger 114 is effected by a motor 38 which rotates a shaft 118 joined to plunger 114. Shaft 118 is threaded and disposed within an oppositely threaded member 119 attached to the end of syringe 113 such that rotary motion of the shaft 114 causes linear motion of the plunger 114 through the barrel of syringe 113. Signals indicative of the position of the plunger 114 are fed back to the microprocessor 11 by means of a linear differential transformer 116 mounted to syringe 113 and having an axial passage through which shaft 118 moves. A magnetic core 119 is provided within the portion of shaft 118 which moves axially through the transformer 116 such that a voltage signal proportional to the axial position of the core is thereby generated. Since the axial position of the core 119 corresponds to the axial position of the plunger 114 within syringe 113, the motion of the plunger 114 may be precisely controlled by the computer or microprocessor 11 to deliver controlled amounts of the therapeutic agent to the needle 100.

D. Example applications

EXAMPLE I

The method and system as described above may be used to advantage in delivering a therapeutic agent that comprises a growth factor for stimulating a particular tissue together with a selective inhibitor. The therapeutic agent comprising a growth factor and inhibitor may then be delivered to the target tissue by the computer controlled injection needle as described above. The means by which such a therapeutic agent may be produced is described below.

In the replication of unicellular organisms, where each cell division generates a new individual, proliferation is controlled by the type and supply of nutrients in the medium in which the organisms reside. In the growth and replication of multicellular organisms, on the other hand, the component cells thereof must obey strict control parameters that limit their proliferation in order to produce and maintain the intricate organization of the multicellular body. At any point in time, most of the cells in a multicellular organism may be in a resting, non-proliferative state even though the supply of nutrients are plentiful. The cells of a multicellular organism are intrinsically unable to divide unless they are provided with positive signals from other cells. Many of these positive signals are in the form of cytokines and growth factors which bind to complementary receptors in the plasma membrane of responsive cells to stimulate cell proliferation via a signal transduction pathway. In this way, the negative controls that otherwise restrain growth are overridden.

Most cytokines and growth factors are proteins, although non-protein growth factors also exist, such as steroid hormones which act on intracellular receptor proteins. As of the date of this application, over fifty such protein growth factors have been discovered, and they can be divided into broad and narrow specificity classes. Factors with broad specificity, such as platelet-derived growth factor (PDGF) and epidermal growth factor (EGF), affect many classes of cells. Thus PDGF acts on a number of target cells including fibroblasts, smooth muscle cells, and neuroglial cells. EGF, while acting mainly on epidermal cells, also acts on many other cell types. At the other extreme are narrow specificity growth factors such as erythropoietin whose sole action is to induce proliferation of red blood cell precursors.

The receptors for most growth factors are transmembrane proteins which function as tyrosine-specific protein kinases. The growth factor ligand binds to the extracellular domain of the receptor and causes the receptor to assemble into dimers. The cytoplasmic domains of each adjacent receptor are then able to cross-phosphorylate tyrosine residues on each receptor. The phosphorylated tyrosines then catalyze other phosphorylation reactions in a signal transduction pathway involving a number of other proteins that eventually result in a growth response.

Cytokines and growth factors regulate a number of physiological processes in addition to proliferation, such as the immune response, cellular differentiation, and apoptosis. Cytokines may therefore be of value in the treatment of disease. Proteins such as erythropoietin and granulocyte colony stimulating factor (G-CSF) have been shown to be of therapeutic value because their sites of action are restricted to only one type of cell. Other cytokines, however, although they produce effects which are therapeutically useful by themselves, produce other undesireable effects due to the widespread distribution of their receptors on many cell types. For example, leukemia inhibitory factor (LIF) causes the proliferation of myeloid cells and megakaryocyte precursors, induces the differentiation of myeloid cells, inhibits the differentiation of embryonic stem cells, activates the cholinergic switch of sympathetic neurons, and promotes bone remodeling. Although some of the effects of LIF may be desirable in a given situation, other effects may be detrimental to the organism. LTF is lethal to experimental animals when given in sufficient quantity. If the action of LIF could be restricted to only one cell type, however, such as bone cells, the cytokine would have therapeutic value. Toward this end, investigators have used soluble specificity-determining R factors targeted to cells by means of monoclonal antibodies in an effort to create specific cellular targets for cytokines. (See Economides et al., *Science* 270, 1351 (1995).) This technique is only applicable, however, in the case of cytokines which require an R factor in order to bind to, and cause the dimerization of, the cytokine receptor.

A growth factor or cytokine having a desired effect on an organism is first selected. The cells of the organism upon whom the desired effect is elicited are termed target cells. Other cells of the organism also respond to the growth factor in what will be presumed an undesirable effect, and these cells are referred to as non-target cells. Such non-target cells and target cells are harvested from the organism in preparation for the next step of generating a monoclonal antibody specific for the non-target cells.

The source of the monoclonal antibody may be a normal mouse or, in the case of a human patient, a transgenic animal whose immune cells are engineered to express human immunoglobulin genes. In another embodiment, an animal specially adapted to harbor a human immune system after being irradiated and then injected with human stem cells may serve as the antibody source. In either case, B-cells manufacturing antibodies with the desired binding specificity proliferate when the animal is challenged with non-target cells from the organism. These B-cells may be removed from the animal and cultured as hybridomas. The B-cells are converted into B-cell hybridomas by fusion of the B-cells with myeloma cells. This may be accomplished in the conventional manner, for example, by mixing the B-cells in a polyethylene glycol medium with HPGRT- myeloma cells (ie., deficient for the enzyme hypoxanthine guanine ribosyl transferase) and selecting for hybrids in an HAT medium (ie., one containing hypoxanthine, aminopterin, and thymidine). Individual B-cell hybridomas are then plated out into single colonies, each of which expresses a specific antibody. At least some of the B-cell hybridomas will express antibody directed against antigens specific to the non-target cells (at least vis-a-vis cells responsive to the selected growth factor), while others will express antibodies directed against other antigenic determinants on the patient's cells. Of course, clones of B-cells manufacturing other antibodies also proliferate, since the stimulating non-target cells possess antigenic determinants other than those specific to the non-target cells. After extracting the messenger RNA (mRNA) from the animal's cultured B-cells, a pool of complementary DNA (cDNA) can be synthesized which contains cDNAs encoding antibodies with the desired binding specificity as well as cDNAs encoding antibodies directed against other antigens and cDNAs encoding other gene products. In order to select out the cDNAs encoding antibodies specifically directed against the non-target cells, a subtraction procedure is employed. A second animal with a genetically identical immune system is challenged with target cells from the same organism to generate B-cells with mRNAs encoding antibodies which bind only to antigens present on the organism's target cells as well as encoding other cellular products unrelated to the antigen. The mRNAs from the target cell challenged animal are mixed with the cDNAs from the non-target cell challenged animal so that hybrids are formed between complementary mRNA and cDNA pairs. The hybrids are then eliminated from the mixture leaving only the unhybridized cDNA from the tumor cell challenged animal. Those unhybridized cDNAs represent the genes for immunoglobulin targeted against the non-target cell specific antigens. The subtraction procedure thus results in the selection of the antibody genes with the desired specificity and eliminated genes for antibodies which would react with the patient's target cells. The selected B-cell genes may then be used as a probe to identify a specific B-cell colony manufacturing antibodies with a specific binding affinity for the non-target cells.

A detailed description of the steps leading to the production of the probes is as follows. First, mRNA is extracted from the B-cell hybridoma colonies in the usual way by lysing the cells and fractionating the RNA from the other cellular macromolecules by means of density gradient centrifugation. The RNA thus extracted contains ribosomal RNA and tRNA in addition to the mRNA which represent the gene sequences actually expressed by the cells, including the gene sequences for immunoglobulin. Owing to the poly-adenine tail at the 3' end of eukaryotic mRNA, the mRNA can be separated by passing the total extracted RNA through a column containing cellulose linked to poly-thymidine deoxynucleotides (or Sepharose linked to poly-uridine nucleotides). The poly-adenine tails of the MRNA hybridize with the thymidine deoxynucleotides so that the mRNA is retained within the column. The mRNA is then eluted from the column with a low salt buffer. Labeled cDNA strands complementary to the mRNA are then synthesized using $^{32}$P-labeled deoxynucleotides and reverse transcriptase, with the RNA being removed by alkaline hydrolysis. This labeled cDNA is then incubated with an excess amount of mRNA extracted from a second pool of B-cell hybridomas. The second hybridoma pool is made from the B-cells of a genetically identical second animal injected with target cells taken from the patient. The mRNA from the second hybridoma pool will only contain sequences which encode immunoglobulin reactive against antigens which are not specific to the patient's non-target cells, as well as mRNA encoding other proteins. Thus all of the labeled cDNA will hybridize with the mRNA except those cDNAs encoding antibody chains specific for non-target cell antigens. The double-stranded hybrids can be removed by passing the mixture through a hydroxylapatite column. The single-stranded cDNA which is eluted from the column will contain sequences complementary to mRNAs encoding heavy and light chains of antibody reactive against the patient's non-target cells. The single-stranded labeled cDNA molecules can then be used as a probe to identify those B-cell hybridoma colonies manufacturing an antibody specifically directed against the patient's non-target cells.

After a hybridoma colony producing the desired monoclonal antibody is selected, a quantity of such antibody is harvested. The antibodies are then conjugated to the extracellular domain of the growth factor or cytokine receptor so that binding of the antibody to non-target cells results in the presentation of a binding site to the growth factor. Methods are well-known to those skilled in the art for covalently linking molecules to immunoglobulins which molecules possess chemically reactive functional groups such as carboxyl, amino, or hydroxyl groups. Such groups are found on nearly all proteins including the extracellular domains of growth factors and cytokines as described herein.

In order to attach a protein molecule with a carboxyl group to an antibody, the carboxyl group is first reacted with an alkylchlorocarbonate under anhydrous conditions so as to form a mixed anhydride. When the mixed anhydride is added to a solution containing the antibody, the anhydride reacts with free amino groups of the immunoglobulin molecule, usually those of lysine side chains, thus forming an amide bond between the antibody and the antibiotic. Protection of free amino groups in the antibiotic molecule prevents undesireable autocoupling. Another method of forming such an amide bond involves first converting the carboxyl group of the antibiotic molecule to an ester which then reacts with a free amino group of the antibody. Reaction of a carboxyl group with a carbodiimide also results in a reactive moiety which forms an amide bond with an amino group. The latter method may also be used to couple the carboxyl group of an antibody to the amino group of an animal antibiotic peptide. Amino groups of antibiotics may also be coupled to immunglobulins using bifunctional reagents which include: 1) heterobifunctional reagents such as N-succinimidyl-3(2-pyridyldithio) propionate which reacts with amino and thiol groups and 2) homobifunctional reagents such as glutaraldehyde which results in a dialdehyde mediated linkage between amino groups of both the antibiotic and immunglobulin occurring via Schiff base formation. Methods for coupling hydroxyl groups of antibiotic molecules to immunoglobulins include: 1) oxidation of primary alcohol groups into carboxyl groups which may then be linked to amino groups as described above, and 2) periodate oxidation of vicinal hydroxyl groups (such as found in antibiotics having glycosidic moietes) to dialdehydes which form Schiff bases with the amino groups of the immunoglobulin molecule.

EXAMPLE II

Hepatocyte transplantation may be used to effect replacement of liver function by injecting a quantity of hepatocytes (contained within a transplant medium such as saline) into an appropriate anatomic site where the hepatocytes are allowed to implant within an extracellular matrix and express differentiated hepatocyte functions. Depending upon the quantity of hepatocytes so transplanted, different degrees of liver function deficiencies may be corrected by replacement of liver function with the cellular transplants. Cellular transplantion of hepatocytes is most advantageous, however, in treating liver disease caused by genetic defects resulting in the absence or decreased function of a single enzyme or other protein product. Such diseases include, for example, the hyperlipidemias and alpha-antitrypsin deficiency. In such cases, a small number of transplanted hepatocytes may be enough to correct the disease by replacing the missing or deficient protein. Such small numbers of hepatocytes can be obtained by a minor wedge liver resection of a living donor who has been tissue matched to the patient. In other applications, greater numbers of hepatocytes may be transplanted and may include hepatic cells which are able to proliferate after transplantation.

In order to perform the transplantation procedure, system 10 is first operated to generate code signals defining digitized images of the patient's body using an appropriate imaging modality or modalities. By analyzing such images, the injection site is selected by user designation (such as by outlining the site with a cursor on a video monitor) of pixels defining the site. Computerized analysis of the image data as described above allows the location coordinates of the selected injection site to be computed, which location coordinates are then applied by the computer to position and actuate the injector. Animal experiments have been conducted whereby hepatocytes have been transplanted both into the spleen and directly into the peritoneal cavity. It has been found, however, that while such cellular transplants are functional and able to carry out bilirubin conjugation, they are not able to survive and function for long periods of time. It is supposed that transplanted hepatocytes need to be exposed to hepatotrophic factors contained in the portal blood flowing to the liver in order exhibit sustained viability and functioning. It is therefore desirable to transplant hepatocytes into the liver parenchyma. In one technique for accomplishing this, the injection site is the patient's spleen. After computation of the spleen's location coordinates, the injector is robotically positioned to inject a transplant medium containing hepatocytes into the spleen. The transferred hepatocytes then meigrate via the splenic vein into the liver parenchyma (See Gupta et al., *Seminars in Liver Disease* 12, 321 (1992)). In another technique, branches of the portal vein are imaged by, for example, CAT scanning of the abdomen after injection of a radioopaque contrast medium. The location coordinates of the portal branches feeding the separate lobes of the liver may then be used to inject the transplant medium into a portal branch and thus infuse a specific liver lobe with hepatocytes. Such selective infusion allows continued portal blood flow through the other liver lobes and prevents possible complications due to occlusion of the portal blood supply by transplanted cells.

EXAMPLE III

In another application of the present invention, heart muscle cells are injected into the myocardium of a patient's heart by the operation of system 10. The appropriate injection site, such as a select region of the ventricular myocardium, is imaged using one or more of the imaging modalities described above. The location coordinates of the injection site are computed, and the injection needle is robotically inserted into the patient's mediastinum and then into the myocardium using the computed location coordinates. After injection into the heart muscle, the transplanted cells interconnect with existing cardiomyocytes both electrically and mechanically by forming gap junctions and desmosomes, respectively. The transplanted cardiomyocytes are then able to at least partially correct deficiencies in pumping function brought about by previous heart cell death due to injury or disease. In order for the transplanted cells to be better capable of invading the myocardium, cellular transplants that exhibit replicative capacity may be employed. Such cells may be obtained from fetal donors or genetically engineered to retain the capability of dividing. Heart muscle cells genetically modified so as to express angiogenic growth factors may also be employed. Such growth factors act to induce the formation of additional blood vessels supplying the myocardium and thus alleviate ischemia resulting from occlusive blood vessel disease.

EXAMPLE IV

One or more of the automatic medical manipulators described above may also be employed to operate on and repair bone in the body of a living being by cutting and/or ablating select portions thereof with a laser and/or by disposing select quantities of fluent bone material mixed with collagen or other organic matter to replace diseased or injured bone, fill in cavities in bone, etc. The described manipulator supporting the described tube or needle may be employed to apply select fluent bone matter made up of cultured osteoblasts in vivo to replace injured, malformed or diseased bone which may be surgically removed as described, wherein the bone mixture ejected from the opening in the needle or tube solidifies or sets in place and eventually becomes part of the bone to which it is applied. Laser light passed through and out the end of the needle or tube as described above, may also be employed to operate on and ablate select bone, such as diseased or injured bone and/or to effect radiation setting or polymerizable material in the mixture or applied to select bone as described to adhere the ejected bone mixture to the bone to which it is applied. An auxilliary manipulator or gripper supported by surgical tool manipulator may be automatically operated as described to handle and hold select tissue during a computer controlled surgical or cell-transplant operation.

The present invention may also employ drug units comprising one or more natural antibiotics or cell-killing agents such as peptides found in such animals as sharks, frogs, moths, jellyfish, lizards or the like, or synthesized or cloned versions thereof. Such agents include peptides such as magainins produced by frogs, cecropins produced by silk moths, defensins found in mammalian small intestine, and steroids such as squalamine derived from dogfish sharks or the like. Small quantities of such peptides or biological agents are delivered by select targeting elements such as monoclonal antibodies to which are attached one or more molecules thereof or a biodegradeable microcapsule such as a liposome or particulate carrier containing the antibiotic or peptide. After binding to a select type of cell, such as a cancer cell, the animal antibiotic is released and kills the cell by attacking the membrane thereof.

So-called natural or biologically synthesized animal antibiotics such as magainins, cecropins, defensins, and squalamine have been found to exhibit a killing effect on cells. The term "animal antibiotic" as used herein shall be taken to mean any type of cell-killing substance (eg., peptides, steroids, or other type of secretion) which is found to naturally occur in animals and is either derived directly from the natural source or synthesized by other means. Such substances are believed to play an important role in the animal's immune system for fighting infections and preventing the growth of cancerous tumors. Magainins, for example, are a family of small peptides originally found in frogs which have been found to disrupt the cell membranes of bacteria, as well as areas of cancer cell membranes which resemble bacterial membranes, so as to cause the cell to lyse and die. Similar peptides found in other animals include defensins from mammalian small intestine and cecropins from moths. Another animal derived antibiotic is squalamine, a steroid, found in sharks. It is well known that sharks very rarely get infections or cancer.

If such natural antibiotics are used to treat disease in humans, they must be delivered to the cancerous or infected cells in a high enough concentration so as to confer a therapeutic benefit. The natural clearance mechanisms of the body, however, may act so as to degrade or otherwise eliminate the agent before such a therapeutic concentration can be reached. Also, the antibiotics may exhibit high toxicity to normal cells. One way to overcome these problems in accordance with the present invention is to precisely deliver the agent to a selected site. Another way, which may be used in conjunction with the injection methods described earlier, is to use targeted drug units.

In accordance with the invention, antibiotics are contained in or consist of drug units to which are bound monoclonal antibodies (or portions thereof) having a specific affinity for the targeted cells. Such targeted cells may be cells of a foreign organism such as bacteria, fungi, protozoa, or parasite. Also, some types of cancer cells exhibit antigenic determinants on their surfaces which are not found on other cells in the body, thus enabling cancerous cells to be targeted as well. One example of such a tumor specific antigen is CEA or carcinoembryonic antigen. Many others are known to the art, and cancers caused by viruses are especially prone to exhibit tumor specific antigens which are encoded by viral genes. Virally infected cells also typically exhibit unique antigens on their surfaces (which is how the body's immune system recognizes and destroys the cells in order to rid the body of the virus) so that they can also be targeted.

As used herein, the term "monoclonal antibodies" shall be taken to mean any collection of antibody molecules, or antigen binding fragments thereof, which all react with a single antigenic determinant. Furthermore, the term shall be taken to include such antibodies as are derived from either human or animal sources (eg., murine monoclonal antibodies), derived from hybridomas transfected with either human or hybrid genes from both animal and human sources (ie., so-called chimeric antibodies), and those antibodies produced as a result of hybridoma technology or otherwise such as the expression of cloned immunoglobulin genes in other types of cells. The term "specific binding affinity," when used to describe a monclonal antibody, shall be taken to mean only relative specificity and not to imply the absence of any cross-reactivity.

Agents such as magainins, cecropins, defensins, or squalamine may be administered to the bodies of patients by means of drug units comprising one or more of such agents and targeting elements such as monoclonal antibodies targeted to specific cells such as specific cancer cells which may be injected in the bloodstream where they target select cells or other matter such as bacteria, virally infected cells, cancer cells, protozoa, or other organisms. Such drug units may comprise intermediate carriers for containing the antibiotic agents which carriers may be in the form of microparticles, cells, liposomes, or other biodegradeable microcapsules. Further, the carriers may be disposed in or mixed with a biodegradeable adhesive which mixture is applied to select tissue such as the wall of the stomach, intestine, organ or vessel leading to or from the organ or a blood vessel or artery to be slowly released therefrom after the adhesive sets to flow therefrom to the bloodstream or be absorbed through the wall thereof to either prevent the onset of a select disease such as cancer and/or destroy select cancer cells, harmful bacteria, fungus or other biological matter in tissue and/or body fluid such as blood.

In one form, the intermediate carrier is a particulate carrier such as a polymeric microparticle or nanoparticle to which is attached one or more monoclonal antibodies or fragments thereof containing the antigen binding region (ie., the $F_{ab}$ fragment). Polymeric nanoparticles may be constructed of such materials as polymethylmethacrylate, polystyrene, and the like, which particles may be readily loaded with the antibiotic. In order to achieve target cell specificity, monoclonal antibodies are coupled to the particle either by direct adsorption of the antibody molecules onto the surface of the particle or by means of a covalent bond.

In the latter case, the particles should possess functional groups on their surfaces that can react with proteins (ie., immunoglobulins) such as aldehyde groups which can directly react with primary amino groups. Other types of functional groups capable of being covalently linked to proteins include carboxyl, hydroxyl, amide, and pyridine groups which can either be directly linked to the antibody or modified to yield reactive aldehyde groups.

In another form, the intermediate carrier is a liposome. Liposomes are container-like structures comprising phospholipids held together by non-covalent forces so as to form a membrane. The use of liposomes as a drug carrier presents several advantages: 1) a relatively large amount of the antibiotic can be encapsulated, 2) the antibiotic is protected from premature inactivation during transport to the target site, and 3) the liposome protects the body from the toxic effects of the antibiotic until it is released. As described below, the liposomes are conjugated to monoclonal antibodies having specific binding affinity for the target cell. After binding to the target cell, the liposome either releases its contents at the cell surface or is internalized into the cell by membrane fusion or endocytosis. Liposomes can be constructed so that they become unstable and fuse with endosomes at the normal endosomal pH of 5–6.5. In this manner, the liposome releases its contents into the target cell's cytoplasm before the contents have a chance to be degraded by lysosomal enzymes. Immunoconjugated liposomes can also be constructed so as to be target sensitive so that they degrade upon binding to the target cell and release their contents of antibiotic at the cell surface. This can be especially desireable in the case of antibiotics such as magainins which exert their killing effect by disrupting the membrane of the target cell. Alternatively, since liposomes can be constructed with varying degrees of stability depending upon their constituent lipids, the liposome may be constructed so as to degrade at approximately the same time that a maximum number of liposomes will be bound to their target cells.

Liposomes may be chemically coupled to monoclonal antibodies either by noncovalent or covalent means. Noncovalent associations may be produced by simply mixing antibodies with liposomes which include as their constituents charged lipids such as phosphatidic acid or stearylamine. Alternatively, biotin-avidin coupling may be employed where advantage is taken of the strong binding affinity the protein avidin has for the coenzyme biotin. In that case, biotin is chemically coupled to one of the components (either the liposome or the antibody) and avidin is coupled to the other. In order to covalently couple antibodies to liposomes, the lipid constituents of the liposome must include lipids having reactive groups capable of conjugating with the reactive moieties of proteins (ie., amines, carboxyls, sulfhydryls, and hydroxyls) or with bifunctional reagents which are coupled to the protein moieties. Such reactive groups found in lipids include amines (eg., phosphatidylethanolamine), carboxyls (eg., free fatty acids), hydroxyls ( eg., phosphadityl serine), carbohydrates ( eg., glycolipids), and phosphates (eg., phosphatidic acid). It is considered preferable to utilize the sulfhydryl moieties of the antibody molecule for conjugation because lipids may then be attached to the free sulfhydryls produced from dissociation of the disulfide bonds holding the light and heavy chains of the antibody molecule together. Conjugation at those sites are much less likely to disrupt the immune reactivity of the antibody molecule since the antigen binding region of each chain will be unaffected. Other types of carriers which may be used for containing animal antibiotics in accordance with the present invention include albumin, dextrans, polyglutamate, polyaspartate, carboxymethylcellulose, and wheat germ agglutinin.

In another form, rather than employing a targeted carrier for containing the antibiotic, the antibiotic is directly conjugated to the monoclonal antibody molecule. Methods are well-known to those of skill in the art for covalently linking drugs to immunoglobulins where the drugs possess chemically reactive functional groups such as carboxyl, amino, or hydroxyl groups. Such groups are found on nearly all proteins including the peptide animal antibiotics described herein.

In order to attach an antibiotic molecule with a carboxyl group to an antibody, the carboxyl group is first reacted with an alkylchlorocarbonate under anhydrous conditions so as to form a mixed anhydride. When the mixed anhydride is added to a solution containing the antibody, the anhydride reacts with free amino groups of the immunoglobulin molecule, usually those of lysine side chains, thus forming an amide bond between the antibody and the antibiotic. Protection of free amino groups in the antibiotic molecule prevents undesireable autocoupling. Another method of forming such an amide bond involves first converting the carboxyl group of the antibiotic molecule to an ester which then reacts with a free amino group of the antibody. Reaction of a carboxyl group with a carbodiimide also results in a reactive moiety which forms an amide bond with an amino group. The latter method may also be used to couple the carboxyl group of an antibody to the amino group of an animal antibiotic peptide. Amino groups of antibiotics may also be coupled to immunglobulins using bifunctional reagents which include: 1) heterobifunctional reagents such as N-succinimidyl-3(2-pyridyldithio) propionate which reacts with amino and thiol groups and 2) homobifunctional reagents such as glutaraldehyde which results in a dialdehyde mediated linkage between amino groups of both the antibiotic and immunglobulin occurring via Schiff base formation. Methods for coupling hydroxyl groups of antibiotic molecules to immunoglobulins include: 1) oxidation of primary alcohol groups into carboxyl groups which may then be linked to amino groups as described above, and 2) periodate oxidation of vicinal hydroxyl groups (such as found in antibiotics having glycosidic moietes) to dialdehydes which form Schiff bases with the amino groups of the immunoglobulin molecule.

In other embodiments, the described so-called natural or biologically synthesized animal antibiotics, magainins, cecropins, defensins, squalamine, and other peptides which are effective in preventing or curing such diseases as cancer or infectious diseases caused by viruses and bacteria, may be administered to the bodies of living beings as follows:

1. Such synthesized animal antibiotic or peptides may be stored and controllably released from an implant such as an ingested or surgically implanted capsule disposed in tissue or a body duct to flow continuously or intermittently released as select quantities thereof in a carrying fluid to either prevent the onset or spread of a disease such as cancer and/or destroy disease cells such as cancer cells after directly flowing or being targeted thereto with monoclonal antibodies or the like as described. Release of such select quantities at select time intervals may be effected by chemical or biodegradeable means or under the control of an electronic microprocessor.

2. A modified form of implant operable to release its contents of one or more animal antibiotics contains a biodegradeable adhesive which becomes activated or released from storage in or adjacent the implant housing and bonds such housing to the blood vessel, stomach or intestinal wall so as to retain the capsule in place for an extended period of time, while its antibiotic or peptide contents or drug units containing same are released to prevent, control or cure the disease, cancer or disease causing bacteria, etc.

3. An organ such as a gland which is derived from a living being such as a frog, shark, jellyfish, pig, goat, cow or other animal which naturally grows same or is caused to grow one or more of such organs by one or more biological engineering techniques or surgery is removed from such animal and is surgically transplanted in tissue, such as the wall of an artery, stomach, intestine, or other organ of a living being. The gland naturally manufactures and secretes the desired peptide or medical material over time which prevents a disease such as cancer from forming in the body. For example, the gland or glands which produce squalamine in sharks may be removed therefrom and used per se or biologically treated before transplanting same in the body of a human to continue to secrete such peptide and dispense same in the bloodstream to prevent tumors and cancers from forming and/or growing in the body of the transplanted.

4. Organs, such as glands operable to form and secrete one or more peptides which, on release therefrom, operate to prevent the initiation or growth of cancer and/or fight or prevent other diseases, may be biologically engineered or cloned and grown using biotechnology techniques and grown to a select degree of maturity whereafter they are surgically transplanted into select tissue or body duct of a living being. The secretion thereafter of the desired peptide from the organ to the body may operate, as in a shark or other animal, to prevent the initiation, growth or spread of cancer and/or to cure previous cancers.

5. Implants, such as surgically implanted capsules and the like, may be operable to contain and controllably release select quantities of a biologically reproducible medication such as one or more of the described peptides or antibiotics which are operable to be grown or reproduced within the implant or one or more chambers thereof Body fluid(s) absorbed through an opening or membrane of the implant may be employed as nourishment for growing or replicating the antibiotic or peptide. Control may be effected by an on-board computer controlling the operation(s) of one or more values of the implant to receive body fluid and release peptides. Living cells may also be used as reservoirs and operate to absorb and release peptides grown therein.

6. A mixture of a bioadhesive and an animal antibiotic encapsulated by a biodegradeable material is adhered to a body duct or organ. Upon degradation of the encapsulating material, the antibiotic is slowly released into the tissue to which the mixture is adhered.

In another embodiment, the targeted drug units comprise antisense oligodeoxynucleotides contained in either a liposome or particulate carrier which is conjugated to a monoclonal antibody having a specific binding affinity for the targeted cell. After binding to the targeted cell, the drug unit is internalized into the cell by endocytosis. After such internalization, the antisense oligodeoxynucleotides localize in the nucleus where they bind to complementary genomic DNA or messenger RNA. By means of such binding, cellular processes such as transcription of mRNA and translation of mRNA into protein are interfered with. By constructing the antisense oligodeoxynucleotides to have a sequence complementary to viral genetic sequences, the agents exert a specific therapeutic effect on virally infected cells, either killing such cells or interfering with intracellular viral replication. If the antisense oligodeoxynucleotides are constructed with a sequence complementary to DNA sequences unique to cancerous cells such as oncogenes, on the other hand, a specific antiproliferative effect may be exerted. In accordance with the present invention, even more specificity for the cancerous or virally infected cells is obtained by incorporating the antisense oligodeoxynucleotides into targeted drug units as described herein, using liposomes or polymeric particles as carriers. Furthermore, the liposome or particulate carrier serves to increase the concentration of antisense oligodeoxynucleotides in the targeted cells for a given dose by preventing their degradation by serum nucleases. This is also important in preventing untoward side effects of antisense oligodeoxynucleotides on normal cells due to nonsequence-specific binding to other macromolecules.

In another embodiment, a targeted drug unit for treating cancer is constructed which comprises a targeting monoclonal antibody conjugated to a carrier having contained therein an antibody with a binding affinity for cellular receptors for epidermal growth factor (EGF). When cancerous cells are treated with conventional chemotherapeutic agents or with radiation, a reparative response is initiated which involves increased expression of cellular receptors for EGF. The increased binding of EGF to a tumor cell results in an enhancement of the cell's reparative processes which may allow it to survive the effects of the chemotherapy or radiation. An antibody directed against the EGF receptor has been developed by ImClone Systems, Inc. of New York. By binding to the EGF receptor, the anti-EGF receptor antibody prevents the subsequent binding of the normal ligand, EGF. The result is an inibition of the effects of EGF on a cell to which the antibody is bound, which inhibition of EGF may be employed to improve the efficacy of conventional chemotherapy. Normal non-cancerous cells, however, also express receptors for EGF, and these receptors may be important in protecting normal tissues from the toxic effects of chemotherapy. If anti-EGF receptor antibodies are delivered to body tissues in a non-targeted fashion during a course of chemotherapy, therefore, undesireable damage to normal tissues may result. Furthermore, the binding of anti-EGF receptor antibodies by non-cancerous cells lessens the quantity available for binding to EGF receptors on tumor cells which necessitates a larger dose if the desired therapeutic effect is to be achieved. Not only does such a larger dose of anti-EGF receptor antibody result in undesireable effects on normal cells as noted above, but the potential for raising an immunogenic response against the antibody in the patient is also increased. This is especially true where repeated dosages of antibody are employed during a long course of cancer chemotherapy. In accordance with the present invention, therefore, anti-EGF receptor antibodies are incorporated into drug units having conjugated thereto a monoclonal antibody having a specific binding affinity for a tumor specific antigen. The drug unit may comprise a liposomic or particulate carrier as described elsewhere in the specification for containing the anti-EGF receptor antibodies. Such targeted drug units may be employed to deliver the anti-EGF receptor antibodies to the cancerous cells in specific fashion during a course of conventional chemotherapy or radiotherapy. In an alternative embodiment, the drug unit carrier may contain, in addition to the anti-EGF receptor antibodies, quantities of a chemotherapeutic agent. Such chemotherapeutic agent may include any of the various conventional tumoricidal agents known to the art, either alone or in combination, as well as cell killing agents mentioned in this specification such as animal antibiotics.

In another embodiment, targeted drug units containing superoxide dismutase (SOD) or other antioxidants can be used for treating amyotrophic lateral sclerosis (ALS). It has been found that patients suffering from a certain inherited type of ALS (familial ALS) have a genetic mutation resulting in the production of SOD with decreased antioxidant activity. (See Deng et al, *Science,* 261, 1047 (1993).) It is believed that at least some types of ALS (and possibly all) may be caused by free-radical damage to motor neurons in the brain and spinal cord where the cells are unable to protect themselves from intracellular free-radicals generated either metabolically or by environmental toxins. One way to treat ALS is to deliver SOD (and/or similar antioxidant enzymes such as glutathione peroxidase and catalase) to the affected neurons by means of a targeted drug unit as described elsewhere herein. In this manner, a sufficient quantity of SOD is transported inside the motor neuron cells for it to have its desired antioxidant effect. In order to target the drug unit to neurons and not other types of cells, the targeting monoclonal antibody is made to bind to certain growth factor receptors which are mainly expressed by nerve cells such as receptors for nerve growth factor (NGF) or ciliary neurotrophic factor (CNTF). Since the NGF receptor is an internalizing receptor, meaning that the receptor is taken inside the cell by endocytosis when a ligand binds to it, the receptor functions similarly after binding with an antibody linked to SOD. Thus the drug unit would comprise anti-NGF receptor antibody bound directly to SOD or to a carrier containing SOD (and/or similar enzymes) using the methods as described herein.

Another type of targeted drug unit for treating cancer comprises a targeting antibody directed against a tumor associated antigen conjugated to immunostimulatory molecules or to a carrier containing quantities of same. Many types of cancerous cells (both spontaneous and virally induced) express tumor specific antigens on their surface which are recognized as foreign by the body's immune system. Activation of T cells requires ligation of the T cell receptor with specific complexes of processed foreign peptide (ie., antigen) and molecules of the major histocompatibility complex (MHC), either class I MHC molecules in the case of CD8+ cytotoxic T cells or class II MHC molecules in the case of CD4+ helper T cells. Such activation results in the stimulation of CD8+ cytotoxic T cells, which then act so as to cause lysis of the antigen presenting cells, and the stimulation of CD4+ helper T cells, which then manufacture and release increased amounts of lymphokines such as interleukin-2 which cause further stimulation of the cytotoxic T cells as well as stimulating other types of cells. Even though such potentially immunogenic antigens may be presented in the context of MHC molecules by cancerous tumor cells, an effective anti-tumor T cell response is not elicited because the tumor cells lack a costimulatory molecule known as B7. The B7 molecule is a costimulatory ligand normally expressed by so-called "professional" antigen presenting cells (APCs) such as dendritic cells, macrophages, and activated B cells. It has been found, however, that full activation of T cells takes place only when a second costimulatory signal is provided by ligation of the CD28 molecule expressed on the surface of the T cell with the B7 ligand. In accordance with the present invention, quantities of B7 molecules are delivered to cancerous (or otherwise diseased) cells by means of targeted drug units comprising a targeting antibody linked to a carrier such as a liposome or microcapsule containing B7 molecules or directly conjugated to the B7 molecule. The B7 molecules thus delivered are then either expressed on the surface membranes of the diseased cell so as to interact with CD28 molecules on the surface of T cells, or interact in soluble form with the CD28 molecules, in a manner which causes stimulation primarily of CD8+ cytotoxic T cells. Such targeted drug units are constructed in accordance with the methods described elsewhere in the application. The drug unit may be designed so as to release a sufficient quantity of B7 or other immunostimulatory molecules so as to be expressed on a plurality of cancerous cells in the vicinity of the targeted site. In order to farther enhance the efficacy of the treatment, activated T cells obtained from a patient's blood, tissues, or primary cultures which are expanded in vitro are also contained within the drug unit carrier.

Other improvements and modifications to the methods described above may be found in applicant's application Ser. No. 07/717,080 for which the issue fee has been paid, and the disclosure of which is hereby incorporated by reference into the present application.

Although the invention has been described in conjunction with the foregoing specific embodiments, many alternatives, variations, and modifications will be apparent to those of ordinary skill in the art. Those alternatives, variations, and modifications are intended to fall within the scope of the following appended claims.

What is claimed is:

1. A system for delivering a therapeutic agent to a patient comprising:

a computer;

an injection needle device for delivering a fluid agent into a tissue;

an automatic manipulator including a manipulator arm assembly for supporting and operation said injection needle and a power driving device for moving said manipulator arm along multiple axes;

a patient support structure having a support surface;

a power driven device operable under computer control for moving said support surface and said manipulator arm assembly relative to one another to cause the manipulator arm assembly to controllably move said injection needle into select regions of the patient's body;

a scanning system including an imaging device for generating image information of select anatomical regions of the patient's body wherein said imaging device includes an ultrasonic pulse-echo transducing means and an actuator for effecting relative movement between said patient support surface and said imaging device which includes a manipulator arm assembly for positioning said ultrasonic transducer under control of said computer;

a plurality of sensors for sensing the relative positions of said patient support, said manipulator arm assembly, and said scanning imaging device, and generating and feeding coded signals representing the sensed positions to said computer;

a first computer program for calculating location coordinates of select body regions defined by pixels of images produced by said scanning imaging device and using the coded signals representing the sensed relative positions of said patient support means and said imaging device; and a second computer program for calculating location coordinates of said injection needle and determining when said injection needle is located at said select body region into which it is desired to deliver a therapeutic agent.

2. A system in accordance with claim 1 further comprising an electronic display device for displaying images and allowing the designation and inputting to said computer of select pixels of said images that correspond to select regions of the patient's body into which it is desired to dispose said injection needle and deliver said therapeutic agent.

3. A system in accordance with claim 1 wherein said scanning system includes a magnetic resonance imaging device.

4. A system in accordance with claim 1 wherein said scanning system includes a computerized axial tomography scanner.

5. A system in accordance with claim 1 further comprising an actuator for effecting relative movement between said patient support and said imaging device under control of said computer.

6. A system in accordance with claim 1 further comprising a program for automatically controlling movement of said manipulator arm assembly so as to cause the insertion of said injection needle into said select body region at a desired depth.

7. A system in accordance with claim 1 further comprising a program for automatically controlling operation of said injector so as to cause it to inject a predetermined amount of said a therapeutic agent into said select body region.

8. A method for internally delivering therapeutic material into a patient, comprising the steps of:

supporting a patient on a patient support which is relatively movable with respect to an injection tool mounted on a computer controlled manipulator arm to permit the tool to be inserted into select regions of the patient's body under control of a computer wherein said injection tool comprises an injection needle having a conduit therein for flowing a fluid medium containing a therapeutic agent into tissue in which the needle is inserted and an injector for forcing the medium through said conduit;

scanning a select portion of the patient's body with a scanning device so as to generate scanning information relating to select regions of the patient's body;

sensing the relative positions of said patient support, said injection tool, and said scanning imaging device, and generating and feeding coded signals representing the sensed positions to a computer in digitized form;

operating the computer to calculate location coordinates of a select body region requiring treatment and defined by select pixels making of the images produced by said scanning imaging device, using the coded signals to predeterminately and relatively position of said patient support means and said scanning device;

designating and inputting to a computer information defining select pixels of images produced by said scanning device which information represents select regions of the patient's body to which it is desired to deliver select therapeutic material;

calculating location coordinates of said injection device and determining if an operating end of said injection tool is properly located at a select body region into which it is desired to deliver said therapeutic material; and, when so located, operating said injection tool to deliver a select amount of said therapeutic material into said select body region and injecting a medicinal agent into said select body region through a second conduit extending through said injection needle.

9. A method in accordance with claim 8 wherein said imaging device and said patient support are relatively movable with respect to each other, said method further comprising the step of selectively positioning said scanning device under computer control so as cause it to generate images of select portions of the patient's body.

10. A method in accordance with claim 8 wherein said injection tool is a catheter having an outflow port for delivering material to an intraductal or other internal body site into which the catheter is inserted.

11. A method in accordance with claim 8 further comprising the steps of automatically moving said injection tool under control of said computer until said injection device is inserted into tissue of said select body region into which select tissue it is desired to deliver said therapeutic material and automatically injecting a select amount of said medium therein.

12. A method in accordance with claim 11 further comprising the step of computer controlling the amount of therapeutic material injected into said select body region.

13. A method in accordance with claim 8 wherein said therapeutic material comprises cellular hepatocytes.

14. A method in accordance with claim 13 wherein said hepatocytes are injected into the patient's spleen.

15. A method in accordance with claim 13 wherein said hepatocytes are injected into a branch of the patient's portal vein.

16. A system for delivering a therapeutic agent to a patient comprising:

a computer;

an injector assembly comprising an injection needle having a conduit therein for flowing a fluid into tissue in which the needle is inserted and an injector for forcing, a therapeutic agent through said conduit wherein said therapeutic agent is a transplant medium containing cellular transplants;

an automatic manipulator including a manipulator arm assembly for supporting and operating said injection needle and a power driving device for moving said manipulator arm along multiple axes;

a patient support structure having a support surface;

a power driven device operable under computer control for moving said support surface and said manipulator arm assembly relative to one another to cause the manipulator arm assembly to controllably move said injection needle into select regions of the patient's body;

a scanning system including an imaging device for generating image information of select anatomical regions of the patient's body;

a plurality of sensors for sensing the relative positions of said patient support, said manipulator arm assembly, and said scanning imaging device, and generating and feeding coded signals representing the sensed positions to said computer;

a first computer program for calculating location coordinates of select body regions defined by pixels of images produced by said scanning imaging device and using the coded signals representing the sensed relative positions of said patient support means and said imaging device; and a second computer program for calculating location coordinates of said injection needle and determining when said injection needle is located at said select body region into which it is desired to deliver a therapeutic agent.

* * * * *